US010814089B2

(12) United States Patent
Wolfson et al.

(10) Patent No.: US 10,814,089 B2
(45) Date of Patent: Oct. 27, 2020

(54) RESPIRATORY ADAPTER AND METHOD OF USE

(71) Applicant: Temple University—Of The Commonwealth System of Higher Education, Philadelphia, PA (US)

(72) Inventors: Marla Wolfson, Wyndmoor, PA (US); Thomas Shaffer, Chadds Ford, PA (US)

(73) Assignee: TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 125 days.

(21) Appl. No.: 16/094,574

(22) PCT Filed: Apr. 18, 2017

(86) PCT No.: PCT/US2017/028038
§ 371 (c)(1),
(2) Date: Oct. 18, 2018

(87) PCT Pub. No.: WO2017/184546
PCT Pub. Date: Oct. 26, 2017

(65) Prior Publication Data

US 2019/0099578 A1 Apr. 4, 2019

Related U.S. Application Data

(60) Provisional application No. 62/324,034, filed on Apr. 18, 2016.

(51) Int. Cl.
*A61M 16/08* (2006.01)
*A61M 16/20* (2006.01)
(Continued)

(52) U.S. Cl.
CPC ...... *A61M 16/0833* (2014.02); *A61M 16/085* (2014.02); *A61M 16/0816* (2013.01); *A61M 16/0858* (2014.02); *A61M 16/0891* (2014.02); *A61M 16/161* (2014.02); *A61M 16/208* (2013.01); *A61M 2016/003* (2013.01);
(Continued)

(58) Field of Classification Search
CPC .............. A61M 16/08; A61M 16/0833; A61M 16/085; A61M 16/0858; A61M 16/0883; A61M 16/0891; A61M 39/08; A61M 16/208
See application file for complete search history.

(56) References Cited

U.S. PATENT DOCUMENTS

| | | | | |
|---|---|---|---|---|
| 1,737,575 A * | 12/1929 | Drager | A61M 16/104 | 128/203.28 |
| 4,529,003 A * | 7/1985 | Iannuzzelli | A61M 15/02 | 128/200.14 |

(Continued)

*Primary Examiner* — Kathryn E Ditmer
(74) *Attorney, Agent, or Firm* — Riverside Law LLP

(57) ABSTRACT

The present invention provides a respiratory adapter for inhaled media deposition in the lungs and airways. The respiratory adapter provides an inspiratory arm and an expiratory arm, wherein the two arms are joined by a bypass flow bridge. A system of valves, such as one-way valves, directs the flow of gas and media through the respiratory adapter to improve media deposition efficiency and to prevent re-breathing of exhaled gas.

19 Claims, 8 Drawing Sheets

(51) Int. Cl.
*A61M 16/16* (2006.01)
*A61M 16/00* (2006.01)

(52) U.S. Cl.
CPC ............... *A61M 2016/0027* (2013.01); *A61M 2016/0039* (2013.01); *A61M 2016/0042* (2013.01); *A61M 2205/3368* (2013.01); *A61M 2205/584* (2013.01); *A61M 2230/432* (2013.01); *A61M 2230/435* (2013.01); *A61M 2230/437* (2013.01)

(56) References Cited

U.S. PATENT DOCUMENTS 4,903,693 A * 2/1990 Yasue ................. A61M 16/085 128/203.12
5,666,946 A * 9/1997 Langenback ..... A61M 15/0018 128/200.16
6,095,140 A * 8/2000 Poon ..................... A61M 16/08 128/204.18
2005/0139211 A1* 6/2005 Alston .................. A61M 16/14 128/200.14
2005/0247316 A1* 11/2005 Orr ................... A61M 16/0093 128/205.12
2012/0215124 A1* 8/2012 Fisher ................. A61M 16/208 600/532
2012/0325220 A1* 12/2012 Heinonen ......... A61M 16/0891 128/205.28

* cited by examiner

RESPIRATORY ADAPTER AND METHOD OF USE

CROSS-REFERENCE TO RELATED APPLICATIONS

This application is the U.S. national phase application filed under 35 U.S.C. § 371 claiming benefit to International Patent Application No. PCT/US17/28038, filed Apr. 18, 2017, which is entitled to priority under 35 U.S.C. § 119(e) to U.S. Provisional Patent Application No. 62/324,034, filed Apr. 18, 2016, the contents of which are each incorporated by reference herein in their entirety.

BACKGROUND OF THE INVENTION

In recent years, with the development of expensive therapeutics, biomarkers, and tracers for inhaled delivery to the lung, there is a need for improving deposition of these media in the lung while minimizing loss of these media during administration with supplemental flow. Most systems of administering inhaled agents are performed with systems that are used in continuous modes for various time durations. Despite the advent of newer patient or ventilator triggered devices for output only during the inspiratory cycle, there remains loss to media both during inspiration and expiration due to flow through the media reservoir and adjustments to supplemental flow associated pressure and/or volume controlled respiratory assist devices (e.g., ventilators, continuous positive airway pressure machines, etc.).

A typical circuit for administering inhaled agents includes a positive pressure media generator connected by tubing to a patient interface, such as a mask, nasal prongs, or an endotracheal tube, and an exhalation path, such as tubing that allows discharge of the expired gases (e.g., to the ventilator if the patient requires active support, to a mode of the ventilator known as continuous positive airway pressure (CPAP) or to an underwater receptacle known as "bubble" CPAP if the patient requires end expiratory lung volume stabilization, or directly to the environment if the patient is freely spontaneously breathing requiring no additional support). In the situation when respiratory assist devices are used, such as a ventilator or with CPAP, the inspiratory and expiratory tubes are typically connected to the patient interface via a "Y" connector, which contains a port for attaching each of the inspiratory and expiratory tubes, as well as a port for the patient interface, and typically, a port for attaching a pressure and/or temperature sensor.

The media delivery reservoir is usually positioned in the inspiratory arm of the circuit, as close to the patient interface as practical. Clinically, administration time of media is based on visualizing the media reservoir; administration time is stopped when no more media is observed in the reservoir. However, this does not mean that the media has been delivered to the lung. In this regard, whether media delivery flow is triggered by patient or assist devices, there is divergent loss of media from the lung during inspiration and expiration. This occurs even if the devices are triggered "on" only during inspiration because there is entraining of media through the device during continual and adjusted supplemental flow associated with pressure and/or volume supported/controlled respiratory devices. These issues divert device-emitted drug away from the lung and diminishes the amount delivered to the patient. The end effect of these challenges is an unknown amount of actually administered drug as well as under administration of media.

There is a need in the art for improved devices and methods for depositing media into a lung with assistive devices. The present invention meets this need.

SUMMARY OF THE INVENTION

In one aspect, the present invention relates to a respiratory adapter for inhaled media deposition comprising: an inspiratory arm having a first end connectable to a ventilator and a second end connectable to a subject/patient breathing interface; an expiratory arm having a first end connectable to a ventilator and a second end connectable to the subject/patient breathing interface; a bypass flow bridge fluidly connecting the inspiratory arm and the expiratory arm between their first and second ends; a media port positioned in the inspiratory arm between its second end and the bypass flow bridge; and one or more valve positioned in each of the bypass flow bridge, in the inspiratory arm, and in the expiratory arm.

In one embodiment, the one or more valve positioned in the inspiratory arm is a one-way valve between the media port and the bypass flow bridge and directs gas to flow in the direction of the media port. In one embodiment, the one or more valve positioned in the expiratory arm is a one-way valve between the second end of the expiratory arm and the bypass flow bridge and directs gas to flow in the direction of the bypass flow bridge. In one embodiment, the one or more valve positioned in the bypass flow bridge is a one-way valve and directs gas to flow in the direction of the expiratory arm.

In one embodiment, the media port is configured to fit a media reservoir, a media driver, or any combination thereof. In one embodiment, a media reservoir is integrated into the media port. In one embodiment, a media driver is integrated into the media port.

In one embodiment, the connector is a Y-connector. In one embodiment, the adapter further comprises at least one low flow sample port fluidly connected to the inspiratory arm. In one embodiment, the adapter further comprises at least one low flow sample port fluidly connected to the expiratory arm. In one embodiment, the adapter further comprises a sensor selected from the group consisting of: a pressure sensor, a flow sensor, a temperature sensor, an oxygen sensor, a carbon dioxide sensor, a media concentration sensor, and a humidity sensor. In one embodiment, the adapter is disposable. In one embodiment, the adapter is reusable.

In one embodiment, the adapter further comprises a housing encasing the inspiratory arm, the expiratory arm, and the bypass bridge, and having at least four ports to accommodate the first end of the inspiratory arm, the first end of the expiratory arm, the MRD port, and the connector port.

In another aspect, the present invention relates to a respiratory adapter for inhaled media deposition comprising: an inspiratory arm having a first end connectable to a ventilator and a second end connectable to a tube; an expiratory arm having a first end connectable to a ventilator and a second end connectable to a tube; a bypass flow bridge fluidly connecting the inspiratory arm and the expiratory arm between their first and second ends; a media reservoir and driver (MRD) port positioned in the inspiratory arm between its second end and the bypass flow bridge; one or more valve positioned in each of the bypass flow bridge and in the inspiratory arm; a housing encasing the inspiratory arm, the expiratory arm, and the bypass bridge, and having at least five ports to accommodate the first and second end of the inspiratory arm, the first and second end of the expiratory arm, and the MRD port; a connector having a connector port, an inspiratory port, an expiratory port, and one or more valve positioned between the breathing port and the expiratory port.

In one embodiment, the one or more valve positioned in the inspiratory arm is a one-way valve between the media port and the bypass flow bridge and directs gas to flow in the direction of the media port. In one embodiment, the one or more valve positioned in the connector is a one-way valve and directs gas to flow in the direction of the expiratory port. In one embodiment, the one or more valve positioned in the bypass flow bridge is a one-way valve and directs gas to flow in the direction of the expiratory arm.

In one embodiment, the media port is configured to fit a media reservoir, a media driver, or any combination thereof. In one embodiment, a media reservoir is integrated into the media port. In one embodiment, a media driver is integrated into the media port.

In one embodiment, the connector is a Y-connector. In one embodiment, the adapter further comprises at least one low flow sample port fluidly connected to the inspiratory arm. In one embodiment, the adapter further comprises at least one low flow sample port fluidly connected to the expiratory arm. In one embodiment, the adapter further comprises a sensor selected from the group consisting of: a pressure sensor, a flow sensor, a temperature sensor, an oxygen sensor, a carbon dioxide sensor, a media concentration sensor, and a humidity sensor. In one embodiment, the adapter is disposable. In one embodiment, the adapter is reusable.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

DETAILED DESCRIPTION

Figure 1A:
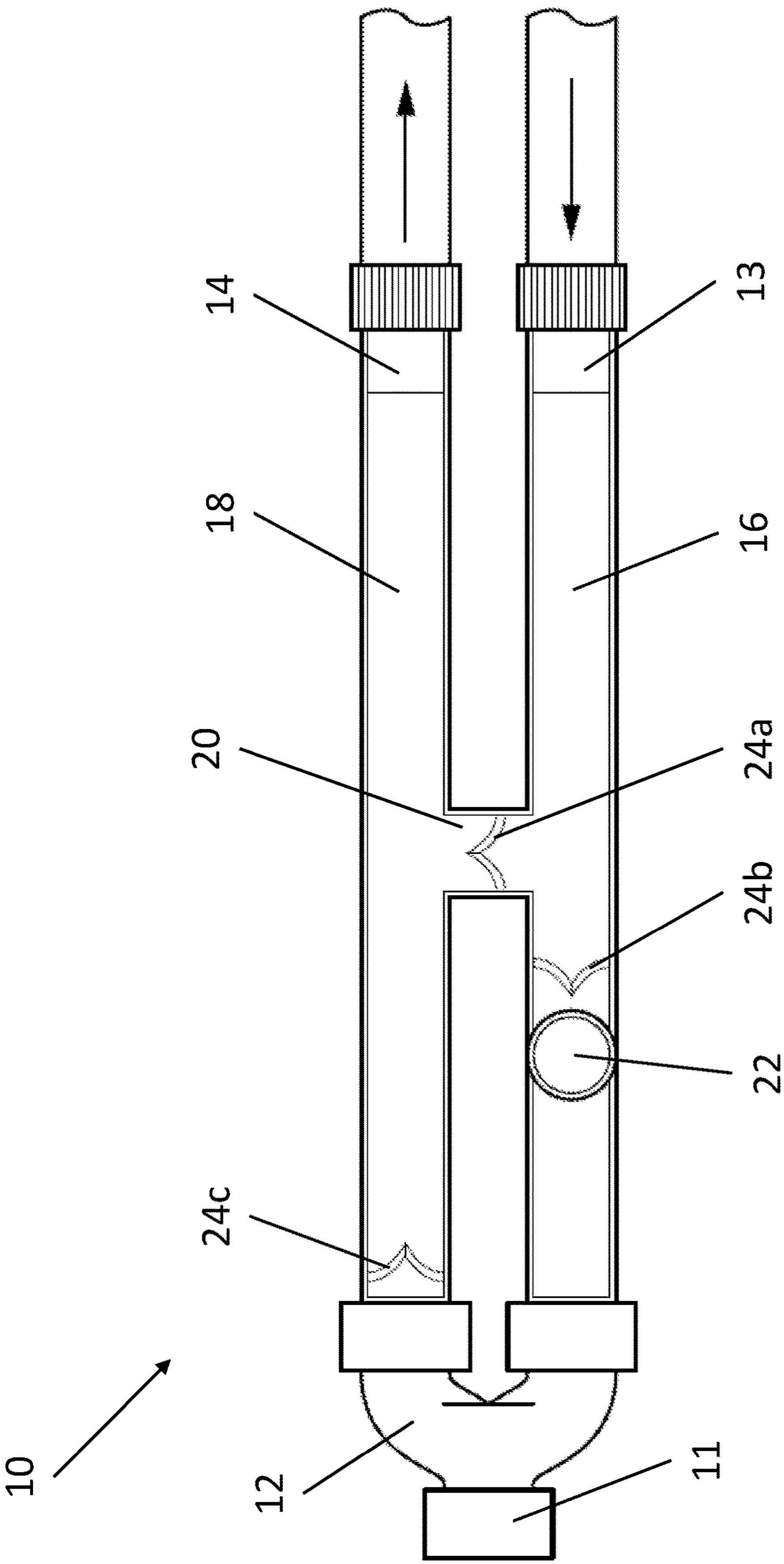
FIG. 1A and FIG. 1B are top-down schematics depicting exemplary respiratory adapter configurations and flow patterns.

The present invention provides a respiratory adapter for inhaled media deposition in the lungs and airway. The respiratory adapter provides an inspiratory arm and an expiratory arm, wherein the two arms are joined by a bypass flow bridge. A system of valves, such as one-way valves, directs the flow of gas and media through the respiratory adapter to improve media deposition efficiency and to prevent re-breathing of exhaled gas.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Respiratory Adapter

There is a widespread need for administering media (e.g., therapeutic or diagnostic) through the inhaled pulmonary pathway. Because of physiologic compensation of the pulmonary circulation to constrict with certain disease states, it is difficult for agents that are given systemically to reach the lungs. To overcome this challenge, systemically administered lung targeted drugs are given at higher than needed doses. The direct pulmonary administration approach provides the greatest opportunity to diagnose/treat the lung or use the lung to enhance delivery of drugs systemically. A wide range of therapeutics, biomarkers, and tracers for inhaled delivery to the lung have been developed for both lung and systemic organ application.

Because of loss through circuit delivering, procedurally, the method of administration to the patient is characterized by the amount emitted by devices, rather than that delivered to the lung, and the "effect" is determined by other assessment methods. For example, despite the advent of patient or ventilator triggered devices for output only during the inspiratory cycle, there remains loss of these media both during inspiration and expiration due to flow through the media reservoir and adjustments to the supplemental flow associated pressure and/or volume controlled respiratory assist devices (e.g., ventilators, CPAP etc.). The present invention addresses the problems faced by conventional respiratory assist methods in at least 3 aspects: 1) greater possibility of administering actual doses, rather than device "emitted doses" to the lung; 2) minimized amounts of media needed, thus providing more cost-effective approaches; 3) minimized loss of media to the circuit and into the environment.

Figure 1B:
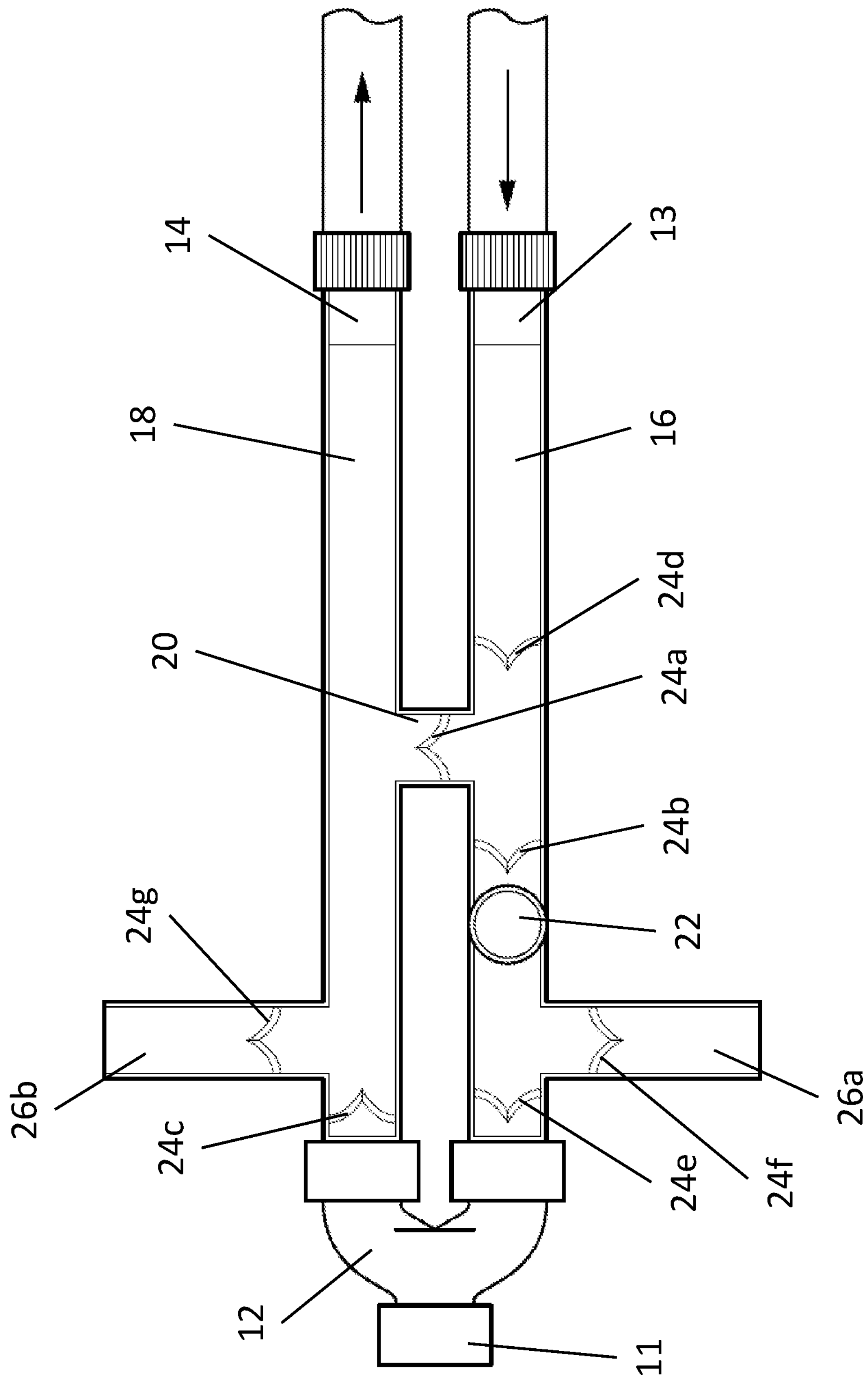

Referring now to FIG. 1A and FIG. 1B, an exemplary respiratory adapter 10 is depicted. Respiratory adapter 10 comprises inspiratory arm 16 having a first end connected to inspiratory port 13 and a second end connected to connector 12, and expiratory arm 18 having a first end connected to expiratory port 14 and a second end connected to connector 12. As will be understood by those having skill in the art, inspiratory port 13 and expiratory port 14 are universal ports that can connect to any respiratory assist device or ventilation system, such as a continuous positive airway pressure (CPAP) or bi-level positive airway pressure (BPAP) machine, or any other driver of gas flow to and from a patient. Connector 12 can be any suitable connector used in the art that connects to a breathing interface to deliver a gas to and from a patient through one or more connector ports 11, such as a Y-connector. It should be understood that the gas can be any gas (such as air, oxygen, therapeutic gas mixtures, and the like), and that gas encompasses all inhaled and exhaled gas mixtures within the context of the present invention. Connector 12 can further comprise any number of valves to control exhaled flow toward expiratory arm 18 (not shown). Inspiratory arm 16 and expiratory arm 18 are fluidly connected between their respective first and second ends by bypass flow bridge 20. A media reservoir and driver (MRD) port 22 is positioned between the second end of inspiratory arm 16 and bypass flow bridge 20. MRD port 22 may be compatible with and be engaged to any suitable media storage and dispensing mechanism commonly used in the art. In some embodiments, a media reservoir and/or driver may be integrated directly into respiratory adapter 10 as a single unit.

Respiratory adapter 10 comprises several valves, such as one-way valves that direct or otherwise permit gas and media flow in one desired direction only. In various embodiments, respiratory adapter 10 has at least one or more one-way valves 24*a* positioned in bypass flow bridge 20. The one or more one-way valve 24*a* directs flow from inspiratory arm 16 into expiratory arm and blocks expired gas from entering inspiratory arm 16 to prevent re-breathing. The one or more one-way valve 24*a* also permits gas to bypass MRD port 22 when a patient is not inhaling, thereby conserving media. In various embodiments, respiratory adapter 10 has one or more one-way valve 24*b* positioned in inspiratory arm 16 between MRD port 22 and bypass flow bridge 20. The one or more one-way valve 24*b* directs flow from the first end of inspiratory arm 16 towards the second end of inspiratory arm 16 and prevents media from escaping into expiratory arm 18 and bypassing a patient during exhalation. In various embodiments, respiratory adapter 10 has one or more one-way valve 24*c* positioned in expiratory arm 18 between the second end of expiratory arm 18 and bypass flow bridge 20. The one or more one-way valve 24*c* directs flow from the second end of expiratory arm 18 towards the first end of expiratory arm 18 and blocks expired gas flow in expiratory arm 18 from returning to a patient during inhalation. In various embodiments, respiratory adapter 10 can further comprise multiple valves 24*d*, 24*e*, or more to supplement flow direction guidance (FIG. 1B).

In some embodiments, the one-way valves of the present invention open mechanically in response to a gas pressure difference across the valve. For example, respiratory adapter 10 can comprise one or more one-way valve 24*b* and/or one-way valve 24*c* having a higher activation pressure than the one or more one-way valve 24*a*. When a patient is in an inspiratory hold, gas flowing into inspiratory arm 16 is at a pressure sufficient to open the one or more one-way valve 24*a* but insufficient to open the one or more one-way valve 24*b*. During inhalation, the pressure drop upstream of media port 22 opens the one or more one-way valve 24*b* while keeping the one or more one-way valve 24*c* closed to direct at least a portion of incoming gas into connector 12. During exhalation, the increase in pressure upstream of media port 22 keeps the one or more one-way valve 24*b* closed while opening the one or more one-way valve 24*c* to direct exhaled gas into expiratory arm 18.

In other embodiments, the present invention uses one- or two-way valves that are electronically controlled. For example, respiratory adapter 10 can comprise valves that are toggled to be open or closed according to a separate controller responding to a breath sensor, synced to a ventilator, or linked to any other respiratory driver. As described elsewhere herein, the valves can be controlled to open and close in a pattern in accordance to in an inhalation phase, an exhalation phase, and an inspiratory hold phase. In the inhalation phase, the valves in inspiratory arm 16 can be controlled to be open, and all other valves controlled to be closed. In the exhalation phase, the valves in expiratory arm 18 can be controlled to be open, and all other valves can be controlled to be closed. In an inspiratory hold phase, the valves in bypass flow bridge 20 can be open, and valves leading to media port 22 can be controlled to be closed. Exemplary one-way and two-way valves include duckbill valves, umbrella valves, ball valves, dome valves. Belleville valves, cross-slit valves, combination valves and the like.

In certain embodiments, respiratory adapter 10 can comprise any suitable sensors, such as pressure sensors, flow sensors, temperature sensors, oxygen sensors, carbon dioxide sensors, media concentration sensors, humidity sensors, and the like. The one or more sensors can be positioned in one or more low flow sample port to measure inhaled or exhaled gas. For example, one or more sensors can be positioned in sample port 26*a* positioned within inspiratory arm 16 to measure inhaled gas composition, or sample port 26*b* positioned within expiratory arm 18 to measure exhaled gas composition (FIG. 1B). The one or more sensors can also be positioned for sensing directly in inspiratory arm 16 and/or in expiratory arm 18. Sample port 26*a* and 26*b* can each have at least one valve 24*f* and/or 24*g*, respectively, to toggle an amount of gas to be analyzed.

Figure 2A:
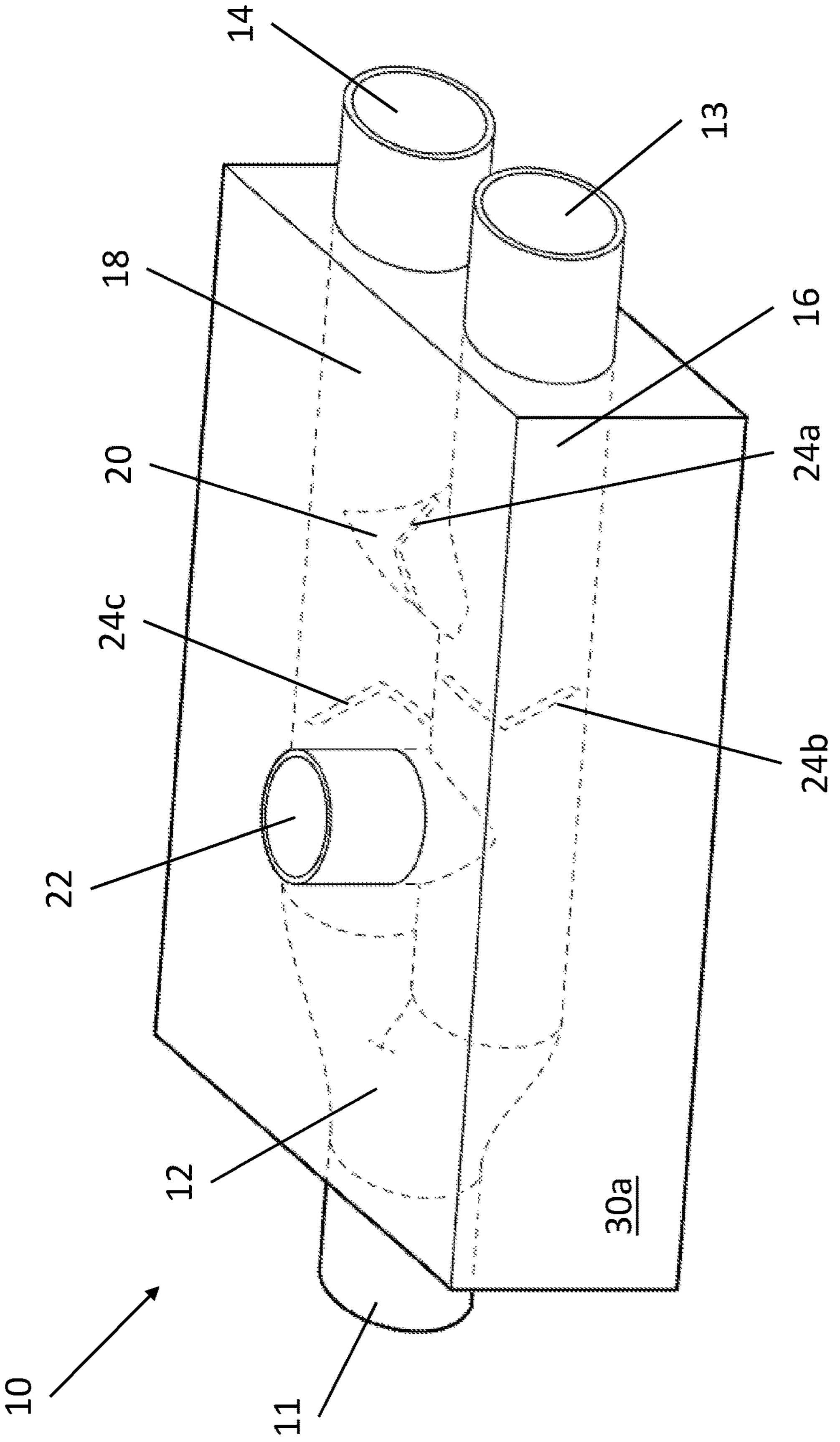
FIG. 2A and FIG. 2B are perspective views of two exemplary respiratory adapters in housing units.
Figure 2B:
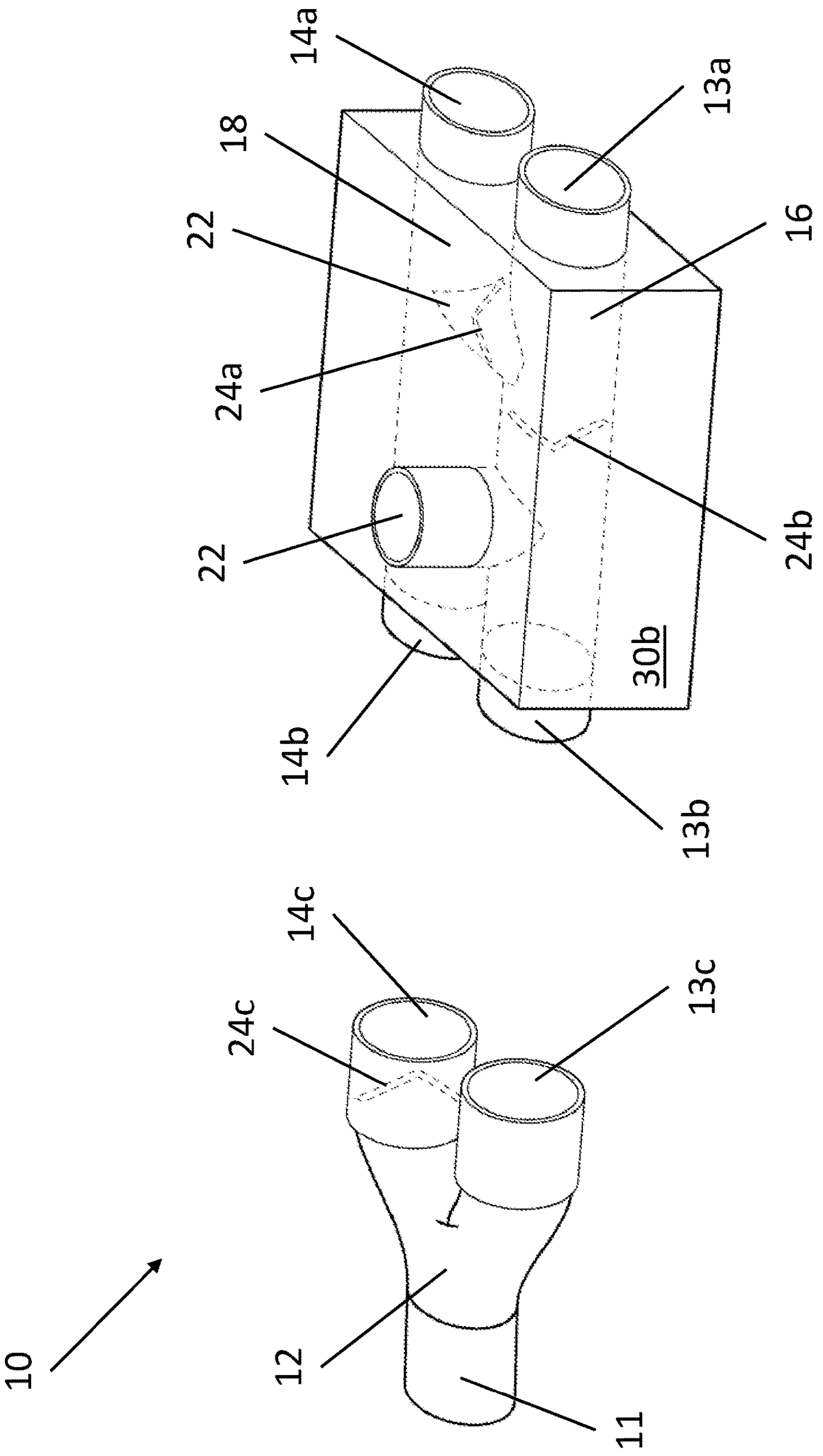

Referring now to FIG. 2A and FIG. 2B, two exemplary configurations of respiratory adapter 10 are depicted. FIG. 2A depicts an all-in-one unit, wherein the entirety of the layout of respiratory adapter 10 are encased within housing 30*a*. Housing 30*a* presents at least four openings corresponding to connector port 11 of connector 12, MRD port 22, inspiratory port 13, and expiratory port 14. FIG. 2B depicts an extendable unit, wherein connector 12, comprising connector port 11, third one-way valve 24*c*, inspiratory port 13*c*, and expiratory port 14*c*, is remote from the rest of the components of respiratory adapter 10 encased within housing 30*b*. Housing 30*b* presents at least five openings corresponding to MRD port 22, inspiratory port 13*a*, inspiratory port 13*b*, expiratory port 14*a*, and expiratory port 14*b*. An extendable respiratory adapter 10 enables inspiratory arm 16 and expiratory arm 18 to be extended by any lengths of tubes connecting inspiratory port 13*c* with inspiratory port 13*b* and expiratory port 14*c* with expiratory port 14*b*. It should be understood that the embodiments depicted in FIG. 2A and FIG. 2B are amenable to any suitable modification for alternative port placement. For example, the various ports can be positioned on any suitable surface of housing 30*a* and housing 30*b*. Housing 30*a* and housing 30*b* can each further comprise one or more additional ports to accommodate one or more additional sample ports. In certain embodiments, respiratory adapter 10 can include one or more labeling features to indicate which port corresponds to inspiration or expiration. For example, housing 30*a* and housing 30*b* may include direct labeling, such as "From Ventilator" for inspiratory port 13*a* and "To Ventilator" for expiratory port 14*a*. Housing 30*a* and housing 30*b* may also include color indicators, such as a clear or white coloring for inspiratory ports 13*a*, 13*b*, and 13*c*, and blue coloring for expiratory ports 14*a*, 14*b*, and 14*c*. Housing 30*a* and housing 30*b* can have any suitable shape, and can include any separable attachment components as desired, such as one or more clips, hooks, hangers, mounting points, and the like. Housing 30*a* and housing 30*b* can be constructed from an opaque material or from an at least partially transparent material. The transparent material can a plastic or glass and can help a user visualize the internal components of respiratory adapter 10 to ascertain orientation or to identify malfunctions.

In various embodiments, housing 30*a* and housing 30*b* package respiratory adapter 10 in a small form factor for enhanced portability. Respiratory adapter 10 can thereby be deployed in any number of uses, such as in the field for military or emergency applications, or in a hospital or home facility. Respiratory adapter 10 and its several components may be disposable or reusable.

The devices of the present invention can be made using any suitable method known in the art. The method of making may vary depending on the materials used. For example, components substantially comprising a plastic or polymer may be milled from a larger block or injection molded. Likewise, components substantially comprising a metal may be milled, cast, etched, or deposited by techniques such as chemical vapor deposition, spraying, sputtering, and ion plating. In some embodiments, the devices may be made using 3D printing techniques commonly used in the art. The ports, connectors, and valves may be of standard or universal designs as would be understood by those skilled in the art.

Method of Use

The respiratory adapter of the present invention is suitable for integration within any respiratory circuit commonly used in the art. As shown in FIGS. 1A and 1B, the respiratory adaptor receives driving flow through inspiratory arm 16 (such as a ventilator) which is connected through a "T" junction to bypass flow bridge 20 and MRD port 22. As described elsewhere herein, bypass flow bridge 20 comprises one-way valve 24*a* to divert flow away from the MRD during inspiration in situations of inspiratory holds, or expiration in situations of variable flow, thereby reducing loss of media from the media reservoir. One-way valve 24*a* also prevents carbon dioxide-rich expiratory flow from the patient from reentering the inspiratory circuit and causing re-breathing of expired gas. One-way valve 24*b* positioned between MRD port 22 and the "T" junction at bypass flow bridge 20 prevents the driving flow from reversing backwards into inspiratory arm 16 at the end of inspiration. This would offset condensation, settling, and eventual loss of media at this point. One-way valve 24*c* positioned in expiratory arm 18 between connector 12 and the "T" junction at bypass flow bridge 20 prevents re-breathing of exhaled gas.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art may, using the preceding description and the following illustrative examples, utilize the present invention and practice the claimed methods. The following working examples therefore, specifically point out exemplary embodiments of the present invention, and are not to be construed as limiting in any way the remainder of the disclosure.

Example 1

Respiratory Adapter Improves Flow Efficiency and Reduces Loss of Media

Figure 3B:
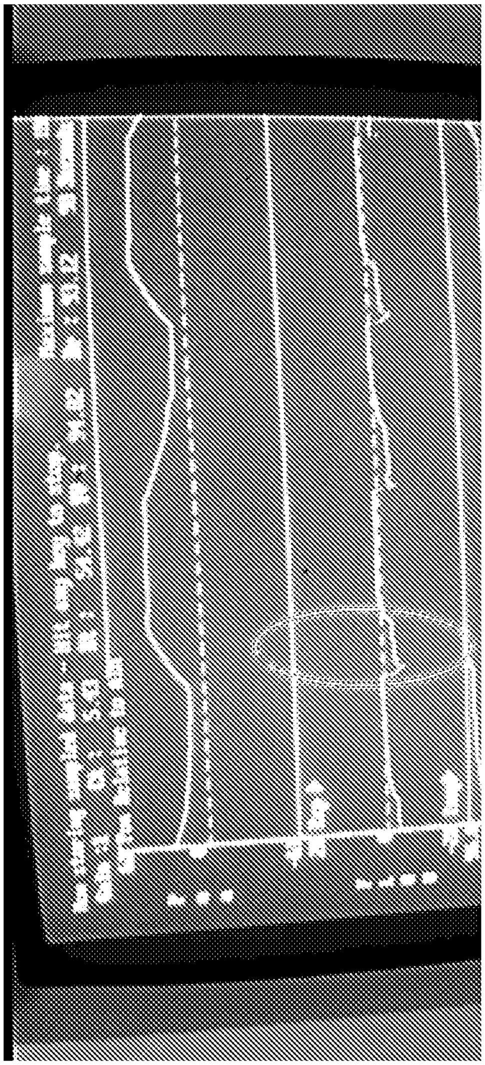
FIG. 3B depicts a monitor screen displaying real-time air-flow tracing in the device of FIG. 3A measured by pneumotachometry.
Figure 3A:
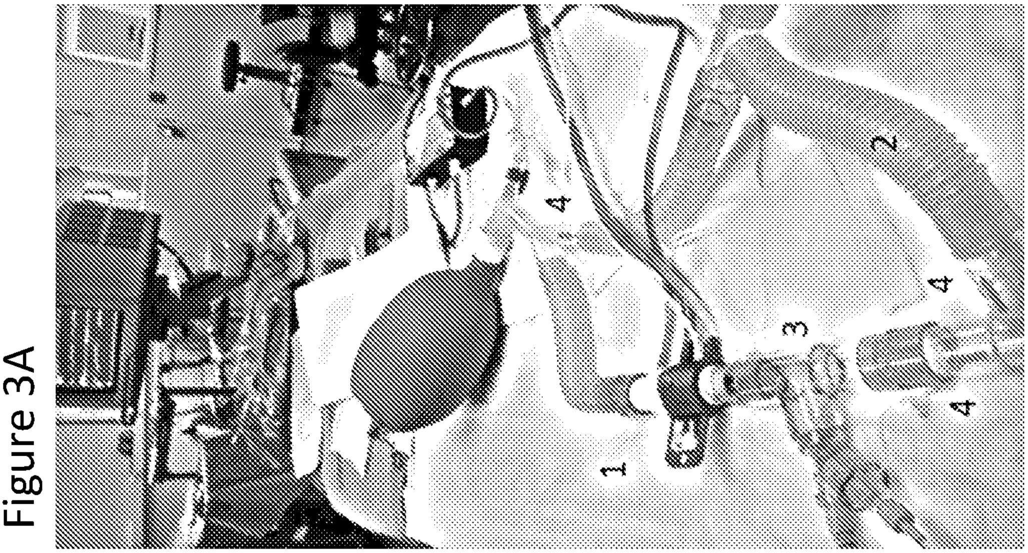
FIG. 3A depicts an experimental respiratory adapter with a pneumotachometer in the inspiratory arm during ventilation of an artificial lung and aerosolization of saline. The components include 1) pneumotachometer, 2) bypass flow bridge, 3) media driver, 4) one-way valve.

Bench top studies were performed using the respiratory adapter with a pneumotachometer at various locations to demonstrate sparing of flow and media contact, which effectively reduces loss of media during both inspiratory and expiratory flow cycles. As shown in FIG. 3A, a pneumotachometer was placed in line with the inspiratory arm, distal to the media generator and bypass flow bridge. As shown in FIG. 3B, this configuration supports flow only in the inspiratory phase. In addition to this configuration, pneumotachometers were placed in two additional locations: the bridge and the expiratory arm distal to the artificial lung (not shown). In these configurations, the flow tracings demonstrated flow and media sparing at the appropriate phases of respiration. For example, when positioned in the expiratory arm, no flow was observed during inspiration as all flow was directed either into the artificial lung or across the bridge. When placed in the bridge, no flow was observed during expiration, demonstrating sparing of flow recycling through the bridge onward through the media driver.

Figure 4B:
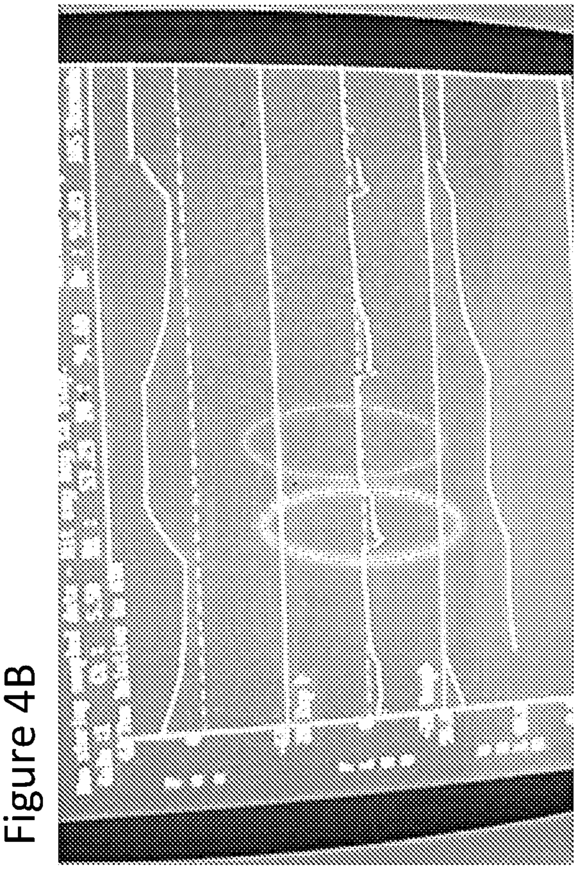
FIG. 4B depicts a monitor screen displaying real-time air-flow tracing in the device of FIG. 4A measured by pneumotachometry.
Figure 4A:
FIG. 4A depicts an experimental respiratory adapter with a pneumotachometer in the bypass flow bridge during ventilation of an artificial lung and aerosolization of saline. The components include 1) pneumotachometer, 2) bypass flow bridge, 3) media driver, 4) one-way valve.

In addition to the configuration in FIG. 3A, the pneumotachometer was positioned in two additional locations: the bridge (FIG. 4A) and in the expiratory arm (FIG. 5A) just distal to the artificial lung. In these configurations, the flow tracings demonstrated flow, and therefore media sparing at the appropriate phases of respiration. For example, when the pneumotachometer was positioned in the bridge, expiratory flow from the artificial lung that traversed the bridge (FIG. 4B, left circle) was "blocked" by the one-way valve at the circled intersection (FIG. 4A) located in the inspiratory line between the bridge and media generator. In addition, when placed in the bridge, no flow was observed during expiration (FIG. 4B, right circle), demonstrating sparing of flow recycling through the bridge onward through the media driver. This demonstrates prevention of expiratory carbon dioxide rich gas from mixing with and/or entering the inspiratory arm, thereby preventing re-breathing of expiratory gas as well as decreasing loss of media by entrainment, thus preserving media within the reservoir.

Figure 5B:
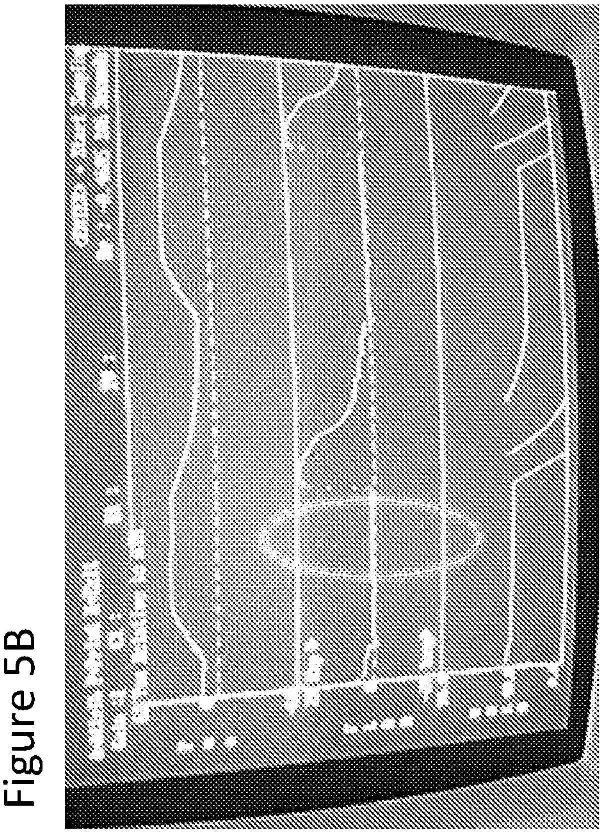
FIG. 5B depicts a monitor screen displaying real-time air-flow tracing in the device of FIG. 5A measured by pneumotachometry.
Figure 5A:
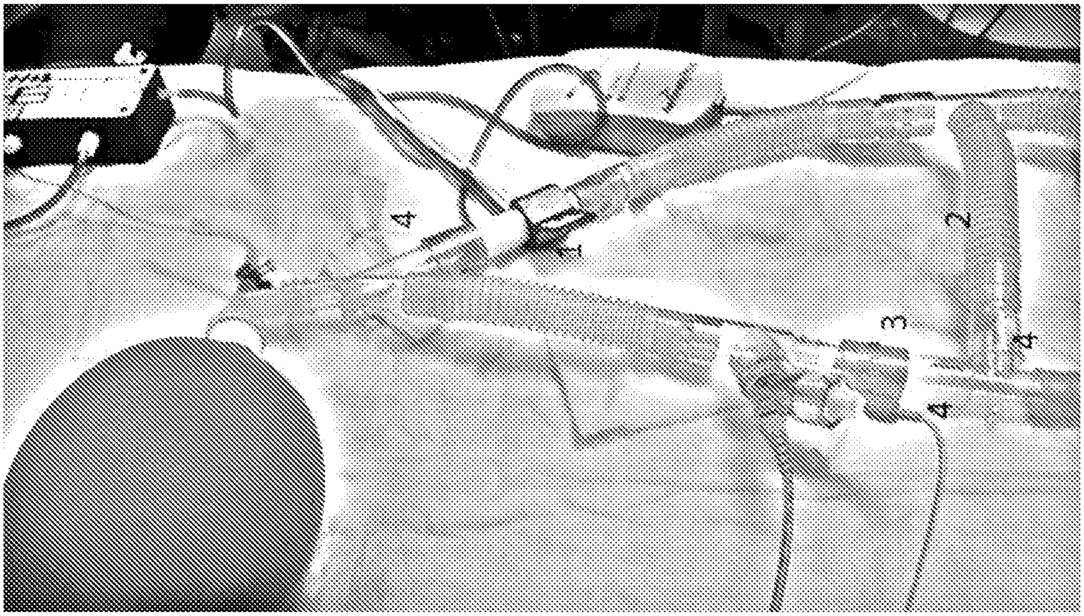
FIG. 5A depicts an experimental respiratory adapter with a pneumotachometer in the inspiratory arm during ventilation of an artificial lung and aerosolization of saline. The components include 1) pneumotachometer, 2) bypass flow bridge, 3) media driver, 4) one-way valve.

As shown in FIG. 5A, when the pneumotachometer was positioned in the expiratory arm, there was no flow observed during inspiration (FIG. 5B, circle; no downward signal on second tracing) demonstrating inspiratory flow directed into the artificial lung with flow occurring only in the expiratory phase. This has the effect of improving the potential for deposition of media from the media generator into the lung during inspiration with loss of media due only to what is exhaled from the lung.

Figure 6B:
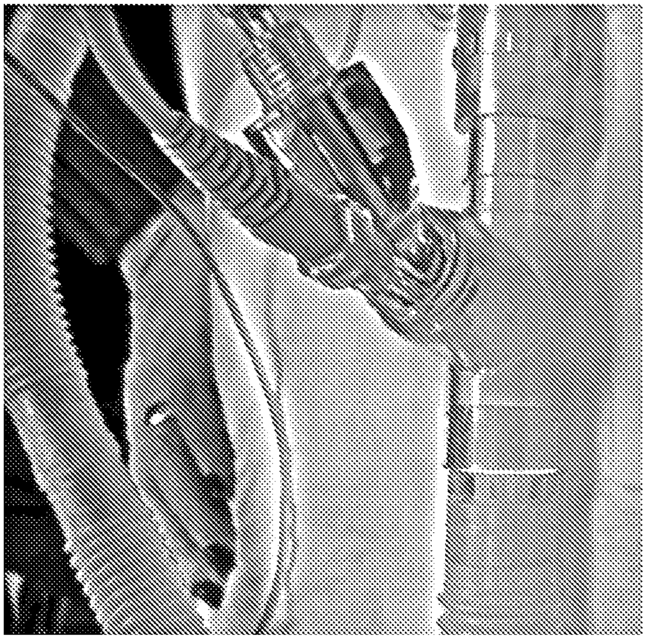
FIG. 6B depicts an experimental respiratory adapter with a bypass flow bridge, demonstrating more sustained aerosolization of emitted media and reduced accumulation in the inspiratory line.
Figure 6A:
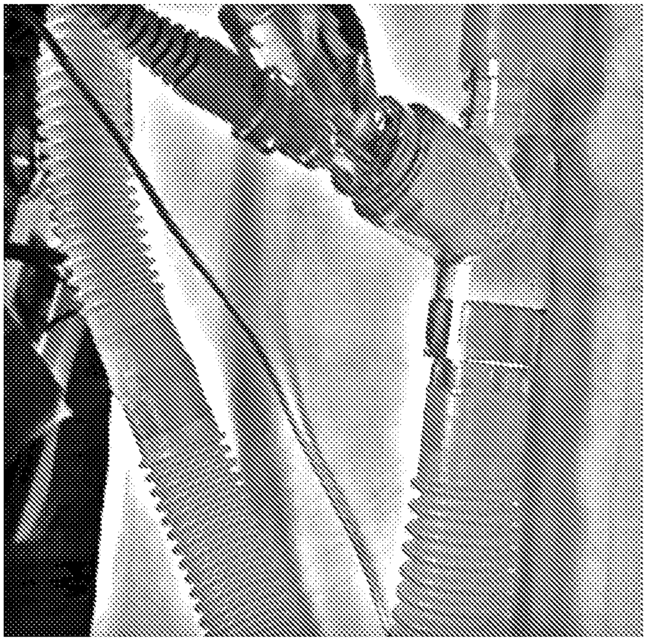
FIG. 6A depicts a conventional respirator without a bypass flow bridge, wherein accumulation of emitted media is visible in the inspiratory line.

As shown in FIG. 6A and FIG. 6B, the respirator adapter has the effect of mitigating the loss of emitted media to the inspiratory circuit itself. These studies were performed with a dye added to the saline, which was then aerosolized without (FIG. 6A) or with (FIG. 6B) the respiratory adapter in place. As shown in FIG. 6A, there was substantial condensation and accumulation of emitted media in the inspiratory line as compared to the respiratory adapter in place. The presence of emitted media in aerosolized form was substantially maintained in the inspiratory flow and accumulation along the walls of the inspiratory line was greatly reduced.

Example 2

A Respiratory Bridge Adapter (RBA) for Improved Inhaled Media Delivery

Despite the use of patient or ventilator triggered aerosol/nebulizer (A/N) devices for delivery during inspiration, media loss remains during both inspiration (I) and expiration (E) due to bias flow through the media reservoir and flow adjustments associated with pressure and/or volume controlled respiratory assist devices. As such, the recommended dose is not delivered and targeted dosing is often "to effect". Furthermore, with the development of expensive therapeutics, biomarkers, and tracers for inhaled delivery, there is an additional economic need for maximizing delivery and deposition of these media in the lung.

The RBA design is based on an (I) and (E) arm, each with a proximal and distal end. A bypass flow bridge connects the (I) and (E) arms near their distal ends and a media reservoir/driver (MRD) port is positioned in the (I) arm between its proximal end and the bypass flow bridge. One-way valves are positioned in the (I) and (E) arms, and the bypass bridge directs flow of gas and media. The RBA design was bench tested with pneumotachometers in the (I), (E), and bypass bridge arms during pressure and/or volume controlled ventilation (neonatal and adult) of an artificial lung and aerosolization of aqueous, dyed media. Flows, pressures and visualization (videography) of aerosol mist were monitored throughout ventilation cycles. Since MRD media delivery efficiency is media property, MRD, and ventilator property specific, in vivo testing of the RBA was performed in parallel with pressure controlled ventilation during continuous aerosolization of saline in an adult sheep hemorrhage/pneumonectomy model, and volume controlled ventilation during ventilator triggered aerosolization of plasminogen activators in an adult sheep smoke inhalation model.

Experimental flow data and videos of aerosol mist patterns demonstrated more sustained aerosolized emitted media, reduced media accumulation in the (I) line, and reduced media loss in the (E) line. Time required to deliver a complete aerosol dose increased (≥25%) due to sparing of media via the (E) limb. Targeted ventilator flows, volumes, and pressures were unchanged with the RBA in-line.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A respiratory adapter for inhaled media deposition comprising:

an inspiratory arm having a first end connectable to a ventilator and a second end connectable to a subject/patient breathing interface;

an expiratory arm having a first end connectable to a ventilator and a second end connectable to the subject/patient breathing interface;

a bypass flow bridge fluidly connecting the inspiratory arm and the expiratory arm between their first and second ends;

a media port positioned in the inspiratory arm between its second end and the bypass flow bridge; and one or more valve positioned in each of the bypass flow bridge, the inspiratory arm, and the expiratory arm, wherein the one or more valve positioned in the expiratory arm is a one-way valve between the second end of the expiratory arm and the bypass flow bridge and is configured to direct gas to flow in the direction of the bypass flow bridge, and wherein the one or more valve positioned in the bypass flow bridge is a one-way valve and is configured to direct gas to flow in the direction of the expiratory arm.

2. The adapter of claim 1, wherein the one or more valve positioned in the inspiratory arm is a one-way valve between the media port and the bypass flow bridge and is configured to directs gas to flow in the direction of the media port.

3. The adapter of claim 1, wherein the media port is configured to fit a media reservoir, a media driver, or any combination thereof.

4. The adapter of claim 1, wherein a media reservoir is integrated into the media port.

5. The adapter of claim 1, wherein a media driver is integrated into the media port.

6. The adapter of claim 1, further comprising a Y-connector connectable to the expiratory arm, the inspiratory arm, and the subject/patient breathing interface.

7. The adapter of claim 1, further comprising at least one flow sample port fluidly connected to the inspiratory arm.

8. The adapter of claim 1, further comprising at least one flow sample port fluidly connected to the expiratory arm.

9. The adapter of claim 1, further comprising a sensor selected from the group consisting of: a pressure sensor, a flow sensor, a temperature sensor, an oxygen sensor, a carbon dioxide sensor, a media concentration sensor, and a humidity sensor.

10. The adapter of claim 1, further comprising a housing encasing the inspiratory arm, the expiratory arm, and the bypass bridge, and having at least four ports to accommodate the first end of the inspiratory arm, the first end of the expiratory arm, the media port, and a connector connectable to the expiratory arm, the inspiratory arm, and the subject/patient breathing interface.

11. A respiratory adapter for inhaled media deposition comprising:

an inspiratory arm having a first end connectable to a ventilator and a second end connectable to an inspiratory port;

an expiratory arm having a first end connectable to a ventilator and a second end connectable to an expiratory port;

a bypass flow bridge fluidly connecting the inspiratory arm and the expiratory arm between their first and second ends;

a media port positioned in the inspiratory arm between its second end and the bypass flow bridge;

one or more valve positioned in each of the bypass flow bridge and the inspiratory arm;

a housing encasing the inspiratory arm, the expiratory arm, and the bypass bridge, and having at least five ports to accommodate the first and second end of the inspiratory arm, the first and second end of the expiratory arm, and the media port;

a connector having a breathing port, the inspiratory port, the expiratory port, and one or more valve positioned between the breathing port and the expiratory port, wherein the one or more valve positioned in the connector is a one-way valve and is configured to direct gas to flow in the direction of the expiratory port, wherein the one or more valve positioned in the bypass flow bridge is a one-way valve and is configured to direct gas to flow in the direction of the expiratory arm.

12. The adapter of claim 11, wherein the one or more valve positioned in the inspiratory arm is a one-way valve between the media port and the bypass flow bridge and in configured to directs gas to flow in the direction of the media port.

13. The adapter of claim 11, wherein the media port is configured to fit a media reservoir, a media driver, or any combination thereof.

14. The adapter of claim 11, wherein a media reservoir is integrated into the media port.

15. The adapter of claim 11, wherein a media driver is integrated into the media port.

16. The adapter of claim 11, wherein the connector is a Y-connector.

17. The adapter of claim 11, further comprising at least one flow sample port fluidly connected to the inspiratory arm.

18. The adapter of claim 11, further comprising at least one flow sample port fluidly connected to the expiratory arm.

19. The adapter of claim 11, further comprising a sensor selected from the group consisting of: a pressure sensor, a flow sensor, a temperature sensor, an oxygen sensor, a carbon dioxide sensor, a media concentration sensor, and a humidity sensor.

* * * * *